(12) United States Patent
Beyer

(10) Patent No.: US 11,723,705 B2
(45) Date of Patent: Aug. 15, 2023

(54) ORTHOPEDIC ROD BENDER

(71) Applicant: Neo Medical SA, La Villette (CH)

(72) Inventor: Morten Beyer, Rød kærsbro (DK)

(73) Assignee: Neo Medical SA, La Villette (CH)

( * ) Notice: Subject to any disclaimer, the term of this patent is extended or adjusted under 35 U.S.C. 154(b) by 163 days.

(21) Appl. No.: 17/286,841

(22) PCT Filed: Nov. 8, 2019

(86) PCT No.: PCT/IB2019/059614
§ 371 (c)(1),
(2) Date: Apr. 20, 2021

(87) PCT Pub. No.: WO2020/095262
PCT Pub. Date: May 14, 2020

(65) Prior Publication Data
US 2021/0346074 A1  Nov. 11, 2021

(30) Foreign Application Priority Data

Nov. 8, 2018 (WO) .................. PCT/IB2018/058786

(51) Int. Cl.
*A61B 17/88* (2006.01)
*A61B 17/70* (2006.01)

(52) U.S. Cl.
CPC ...... *A61B 17/8863* (2013.01); *A61B 17/7086* (2013.01)

(58) Field of Classification Search
CPC .................. A61B 17/7074; A61B 17/8863
See application file for complete search history.

(56) References Cited

U.S. PATENT DOCUMENTS

| | | | | | |
|---|---|---|---|---|---|
| 5,237,847 | A * | 8/1993 | Owens | ..................... | B21D 7/06 |
| | | | | | 72/213 |
| 6,006,581 | A * | 12/1999 | Holmes | .................. | B21D 7/063 |
| | | | | | 72/409.1 |
| 6,644,087 | B1 * | 11/2003 | Ralph | ................ | A61B 17/8863 |
| | | | | | 72/213 |
| 9,144,835 | B2 * | 9/2015 | Houle | .................... | B21D 7/063 |
| 9,314,830 | B2 * | 4/2016 | Tremblay | ................. | B21D 7/06 |
| 10,702,323 | B2 * | 7/2020 | Richards | ............ | A61B 17/8863 |

(Continued)

OTHER PUBLICATIONS

International Search Report dated Mar. 23, 2020, for Application N° PCT/IB2019/059614.

(Continued)

*Primary Examiner* — Eduardo C Robert
*Assistant Examiner* — Steven J Cotroneo
(74) *Attorney, Agent, or Firm* — Nixon & Vanderhye P.C.

(57) ABSTRACT

The present invention concerns an orthopaedic rod bender including: a rod receiving zone configured to receive a first rod having a predefined curvature and a second rod to which a curvature is to be imparted; a first support and a second support for contacting the first rod, the first and the second 9B supports being located on a first side of the rod receiving zone opposite the first side; and a mobile head located on a second side of the rod receiving zone; the mobile head being configured to be displaced towards the first side and in the rod receiving zone to contact the second rod and to apply a force to the second rod to push the second rod towards the first rod to impart a curvature to the second rod.

20 Claims, 9 Drawing Sheets

(56) References Cited

U.S. PATENT DOCUMENTS

| | | | |
|---|---|---|---|
| 2003/0205075 A1* | 11/2003 | Strippgen | A61B 17/8863 |
| | | | 72/173 |
| 2004/0138662 A1 | 7/2004 | Landry et al. | |
| 2004/0144149 A1 | 7/2004 | Strippgen et al. | |
| 2009/0222020 A1* | 9/2009 | Schmuck | A61B 17/8863 |
| | | | 606/205 |
| 2012/0186411 A1* | 7/2012 | Lodahi | A61B 17/8863 |
| | | | 83/639.1 |
| 2016/0346026 A1 | 12/2016 | Bootwala et al. | |
| 2017/0238976 A1* | 8/2017 | Higaki | A61B 17/7032 |
| 2021/0275239 A1* | 9/2021 | Rouge | B21D 7/00 |

OTHER PUBLICATIONS

Written Opinion of the ISA dated Mar. 23, 2020, for Application N° PCT/IB2019/059614.

\* cited by examiner

ORTHOPEDIC ROD BENDER

CROSS-REFERENCE TO RELATED APPLICATIONS

The present application is a United States national stage application of International patent application PCT/IB2019/059614 filed on Nov. 8, 2019 designating the United States, and claims foreign priority to International patent application PCT/IB2018/058786 filed on Nov. 8, 2018, the contents of both documents being herewith incorporated by reference in their entirety.

FIELD OF THE INVENTION

The present invention concerns a rod bender and more particularly an orthopaedic rod bender. The device can be used for bending or bestowing a curvature to a rod, for example, an orthopaedic rod such as that used as an intervertebral connecting element in spinal surgery and placed in the heads of spinal or pedicle screws to interconnect and maintain a plurality of implanted spinal screws in a desired position in vertebrae and the spine of a patient.

BACKGROUND

An orthopaedic rod is placed and held in the heads of a plurality of spinal or pedicle screws implanted in vertebrae or the spine of a patient during spinal surgery.

Such a rod or elongated member is, for example, shown in FIGS. 71 to 74 of patent application US2004/0138662, the entire contents thereof being herewith incorporated by reference. US2004/0138662 also shows spinal or pedicle screws configured to receive and hold such rods in their heads permitting spinal stabilization to be achieved.

The spinal screws in association with the rod are used to correct spinal deformity or to treat spinal trauma. The rod is bent or deformed to define a rod curvature permitting the rod to be placed in each screw head of the plurality of spinal screws to inter-link the plurality of spinal screw heads which are very often non-linearly aligned so as to correct a spinal deformity or to treat a spinal trauma.

Known orthopaedic rod benders require considerable physical force to be manually applied by the user or Surgeon to bend a rod or impart a desired curvature to the rod. Furthermore, the rod may require multiple curvatures to imparted thereto.

The rod must be continually removed from the rod bender, aligned with the curvature defined by the screw heads already positioned in the spine of the patient and re-inserted into the rod bender for further bending or adjustment. This process is repeatedly carried out during the surgical operation by the Surgeon until the curvature of the rod matches the curvature defined by the implanted screw heads or a curvature desired by the Surgeon.

Moreover, known orthopaedic rod benders generate stress in the rod stemming from compressional, tensional and torsional forces applied by the rod bender when bending the rod to match the curvature defined by the screw heads.

SUMMARY

The goal of the present invention is to provide an orthopaedic rod bender that overcomes the above-mentioned inconveniences.

In particular, a goal of the present invention is to provide a rod bender that allows a curvature to be more easily imparted to an orthopaedic rod.

A further goal, is to assure that the stress imposed on the rod during bending is reduced.

The present invention is thus an orthopaedic rod bender according to claim 1.

The rod bender according to the present invention advantageously assures that only tensional forces are generated in the rod during bending and that compressional and torsional forces are eliminated or significantly reduced. This assures that the stress imposed on the rod during bending is reduced or minimized thus assuring that the rod can fulfil its spinal deformity correction function in the body for a longer duration.

The present invention also advantageously allows an orthopaedic rod to be produced by rod replication. A desired curvature to be applied to a rod can be done using a template rod. The template rod can be, for example, consist or comprise a work-hardening material and be manually bent to set a curvature defined by the screw heads. The template rod material is allowed to harden and then used in the rod bender to impart a similar or identical curvature to a second rod, this second rod being destined to be placed and fixed in the plurality of screw heads.

The present invention also concerns an orthopaedic rod bender system including the above-mentioned orthopaedic rod bender, as well as a first template rod and/or a second rod destined to interlink a plurality of pedicle screw-heads.

The present invention also concerns an orthopaedic rod bending method according to claim 21.

Other advantageous features can be found in the dependent claims.

The above and other objects, features and advantages of the present invention and the manner of realizing them will become more apparent, and the invention itself will best be understood from a study of the following description with reference to the attached drawings showing some preferred embodiments of the invention.

A BRIEF DESCRIPTION OF THE SEVERAL VIEWS OF THE DRAWINGS

The Figures show non-limiting and exemplary embodiments of the present invention.

FIGS. 2A to 2D schematically show a rod bender of the present disclosure in which a mobile head is displaced to different positions in a rod receiving zone.

Figure 3A:
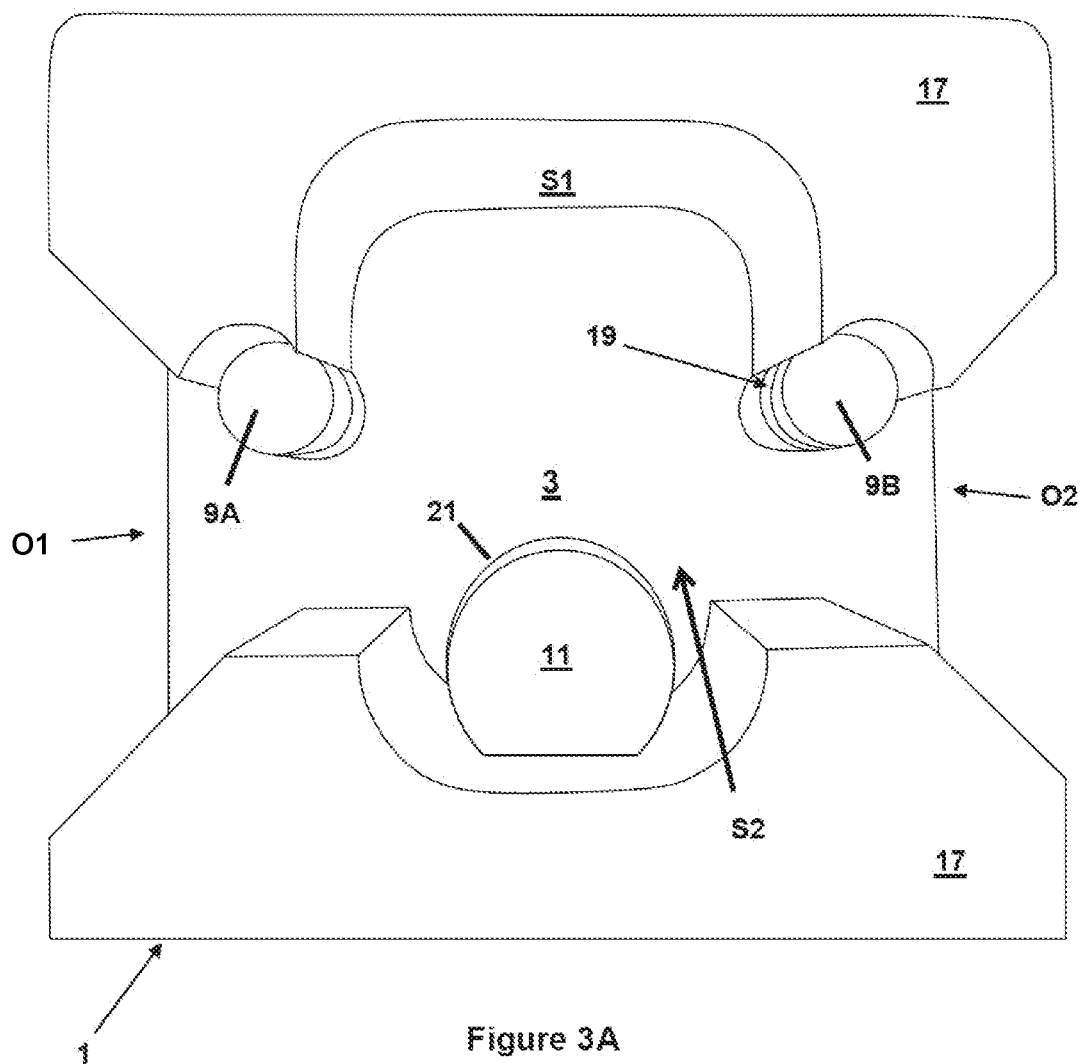
Figure 3B:
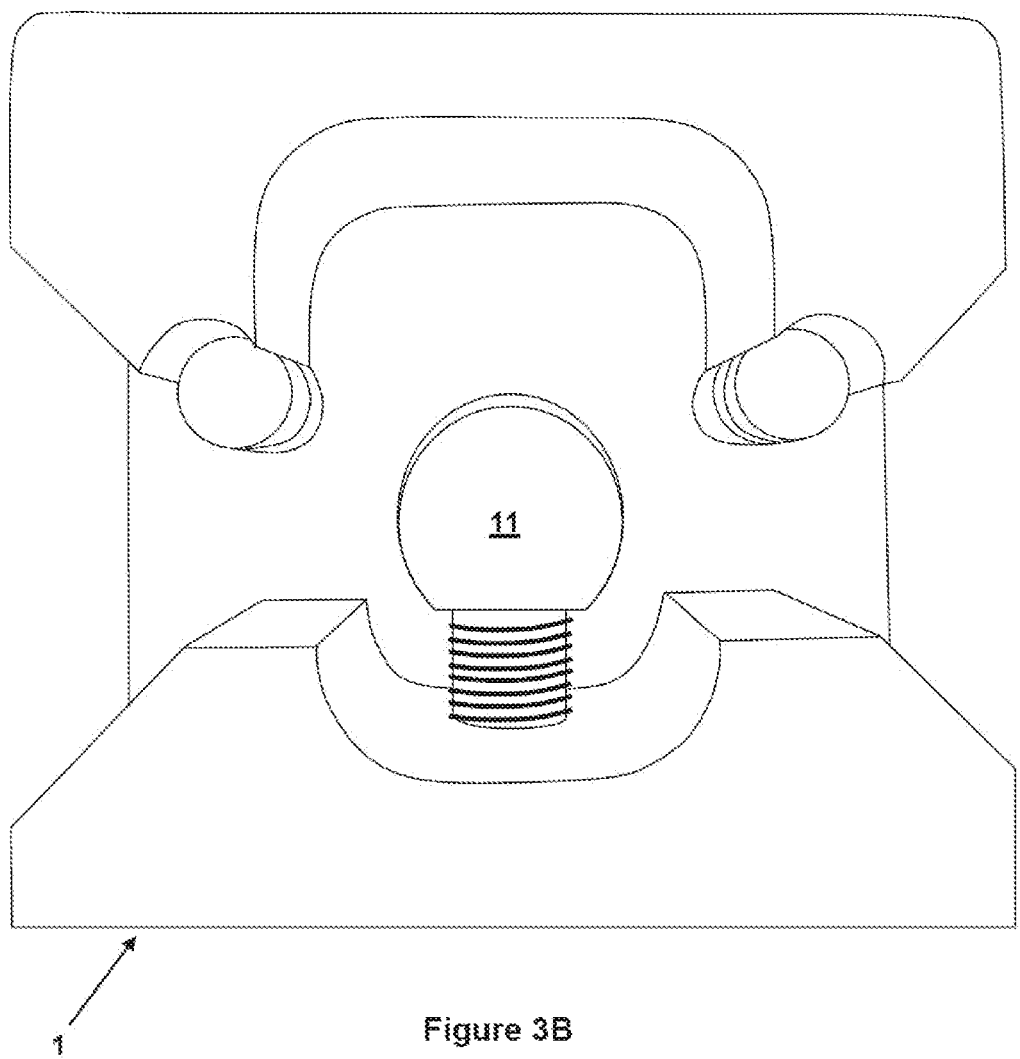
Figure 3C:
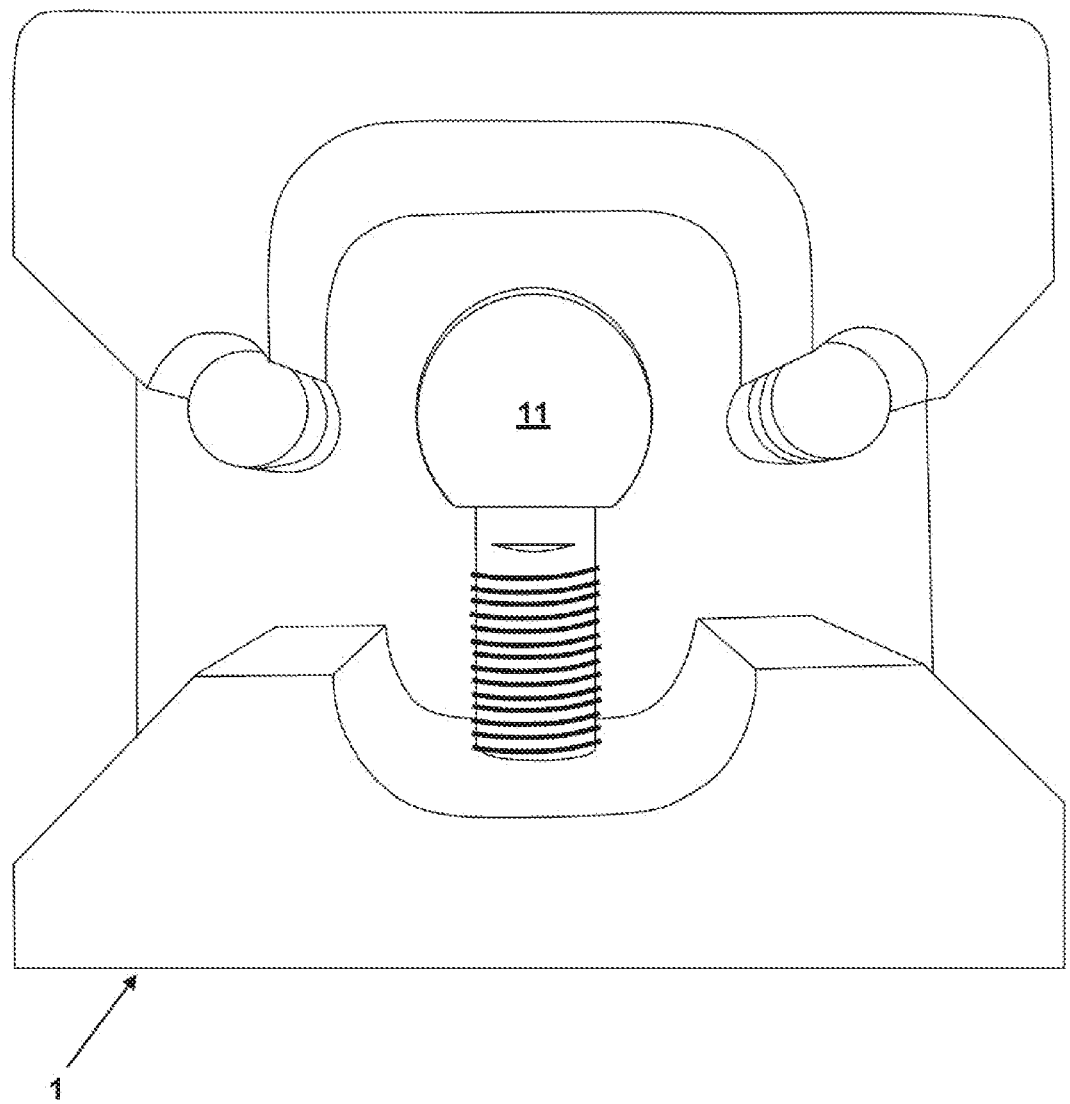

FIGS. 3A to 3C schematically show close-ups or zoomed-in illustrations of a rod bender of the present disclosure in which a mobile head is displaced to different positions in a rod receiving zone.

Figure 4:
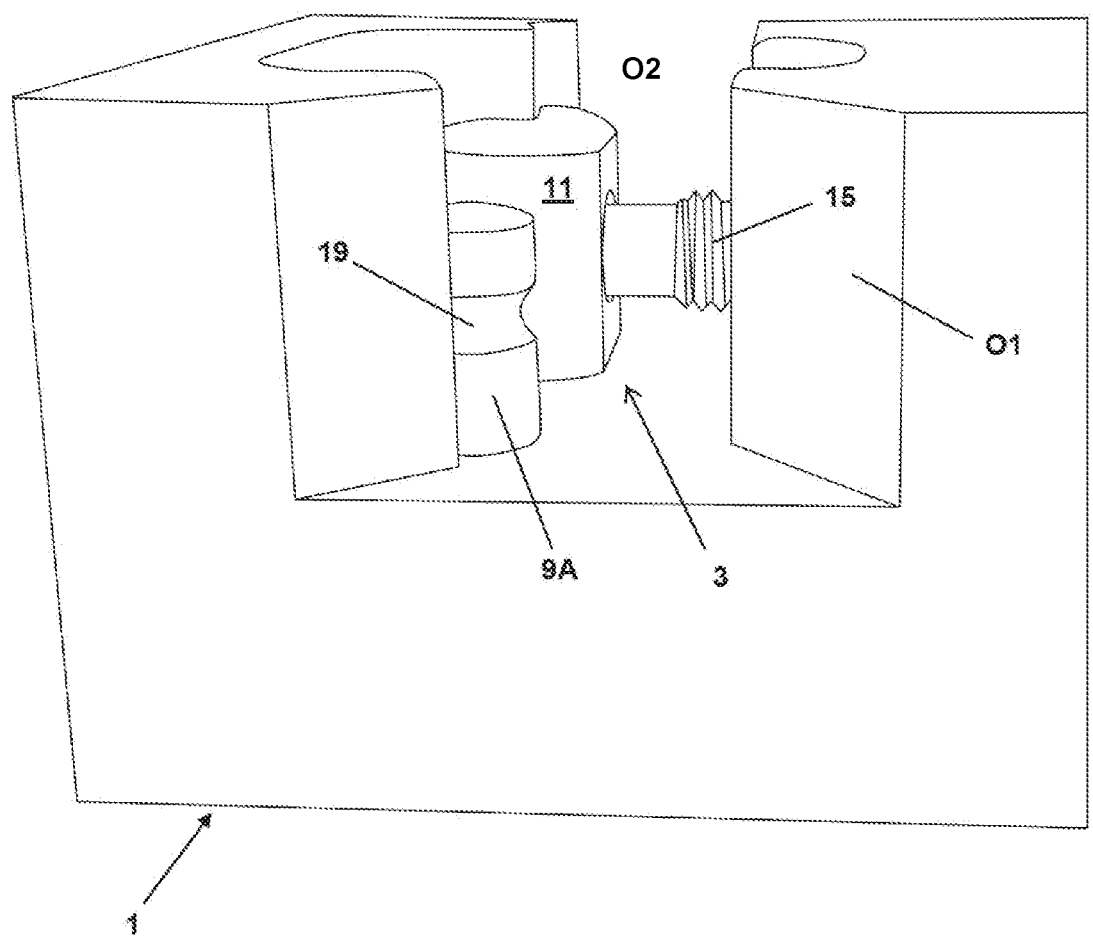

FIG. 4 schematically shows a side-view of a rod bender of the present disclosure.

Herein, identical reference numerals are used, where possible, to designate identical elements that are common to the Figures.

DETAILED DESCRIPTION OF THE SEVERAL EMBODIMENTS

An exemplary rod bender or orthopaedic rod bender according to the present disclosure are shown, for example, in FIGS. 1A, 2A to 2D, 3A to 3C and 4.

Figure 1A:
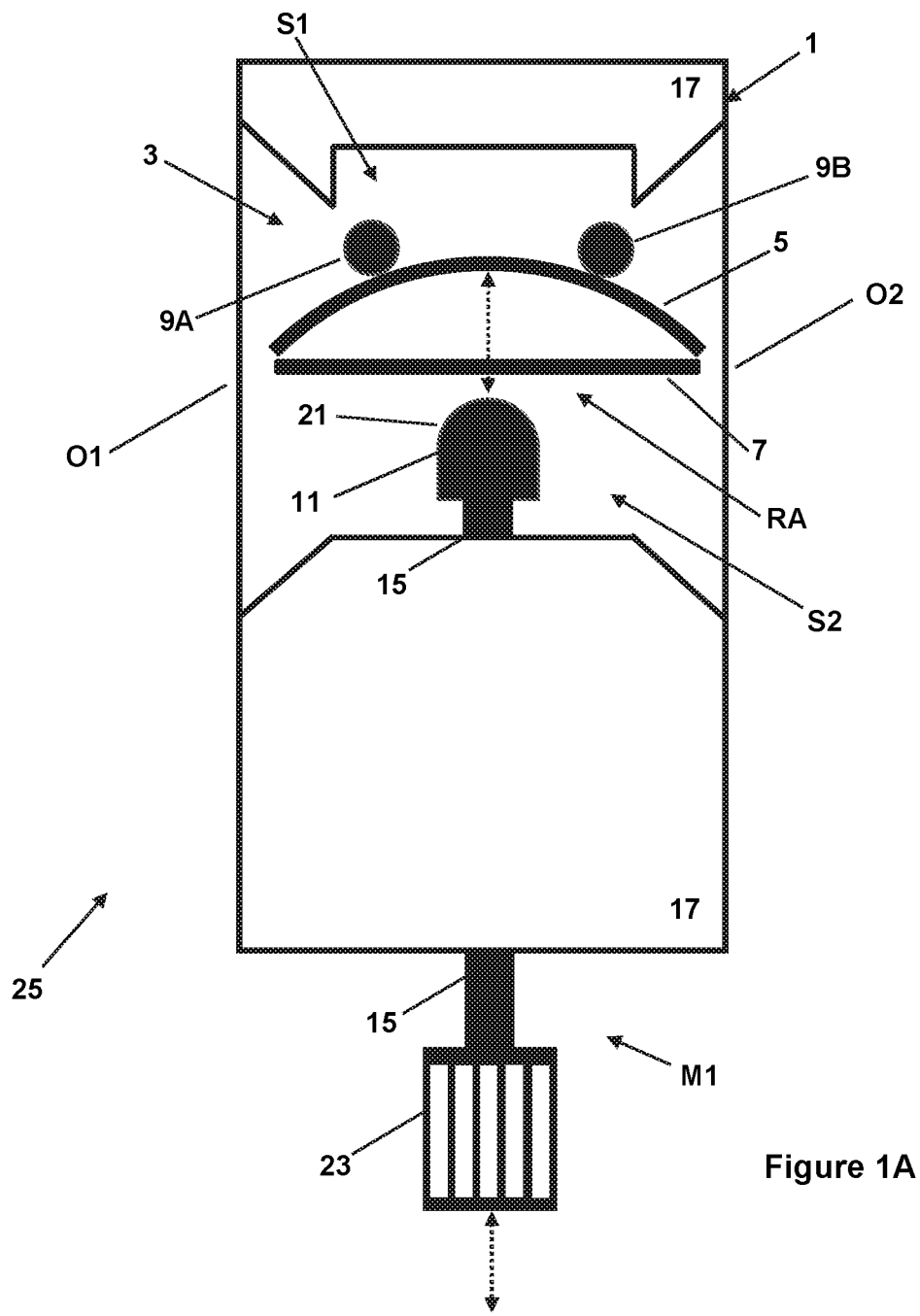
FIGS. 1A, 2A to 2D, 3A to 3C and 4 shows schematically an exemplary rod bender according to the present disclosure.

As shown for example schematically in FIG. 1A, the rod bender 1 includes a rod receiving zone 3 configured to receive a first rod 5 having a predefined curvature and a second rod 7 to which a curvature or contour is to be imparted.

The second rod 7 is an orthopaedic rod and is destined to be implanted in a body or a patient. It is destined to remain in the patient body. As mentioned, the second rod can be used as an intervertebral connecting element in spinal surgery and placed in the heads of spinal or pedicle screws to interconnect and maintain a plurality of implanted spinal screws in a desired position in vertebrae and the spine of a patient.

The second rod 7 is, for example, an elongated member that is configured to be received in a head of a spinal screw or pedicle screw for implantation in the body of a patient. The rod 7 is configured to be received, for example, in the head of a first spinal screw and the head of a second spinal screw. The rod can be maintained in both heads using, for example, a set screw subsequently positioned in each head after insertion of the rod.

The rod 7 has a length that permits the rod to be received in the heads of at least two spinal screws. A width or diameter of the rod 7 is such that it can be received inside a head of an implantable spinal or pedicle screw.

In a non-limiting example, the rod 7 may, for example, have a length of between 30 mm and 300 mm and a diameter or width between 4 and 7 mm.

The rod 7 can, for example, be a straight rod or alternatively be a bent rod.

The rod 7 may have a (substantially) circular cross section in a plane perpendicular to the direction of elongation of the rod, or may have other cross-sectional shapes including an oval, rectangular, rhomboidal or square shape. The rod 7 may also have irregular cross-sectional shapes.

The rod may, for example, define a cylindrical shape. The extremities of the rod 7 may be tapered and/or rounded. One extremity may include an orifice permitting the rod 7 to be attached to an instrument for insertion into the spinal screws.

The first rod 5 may, for example, have the same dimensions, sizes and cross-sectional shape as the second rod 7. Their constituent materials are, in a preferred embodiment, different.

The first rod 5 may comprise or consist solely of a work-hardening material. That is, the first rod 5 can be or is configured to be manually manipulated by a Surgeon to manually bend the rod 5 without a rod bending machine or device to match a curvature, for example, defined by a plurality of pedicle or spinal screw heads implanted in pedicles or vertebrae. The first rod 5 can be configured to be manipulated and contoured by hand. The rod 5 hardens after the manual bending or curvature has been applied by a Surgeon and is placed in the rod receiving zone 3 of the rod bender 1.

The first rod 5 may, for example, comprises or consists solely of aluminum, or copper, or 6061-T6 alloy or 6061-T4 alloy.

The rod bender 1 is configured to apply, to the second rod 7, a matching curvature or corresponding curvature matching or corresponding to that of the first rod 5 (hardened first rod 5). The second rod 7 is destined to be placed for a long-time duration in the spine of a patient or in the heads of the plurality of pedicle screws implanted in a patient (those used to define the curvature to the first rod 5). The second rod 7 is an inter-vertebral linking rod. The first rod 5, comprising a curvature or contour to be transferred to the second rod 7, is harder than the second rod 7 or less malleable than the second rod 7.

The second rod 7, for example, comprises or consists solely of steel, stainless steel or titanium. The rod bender 1 may also include a first support 9A and a second support 9B for contacting or directly contacting the first rod 5. The first support 9A and the second support 9B are located on a first side or upper portion 51 of the rod bender 1 or of the rod receiving zone 3.

The rod bender 1 may also include a mobile head 11 located on a second side S2 of the rod receiving zone 3. The second side S2 is for example opposite the first side 51.

The mobile head 11 is located at an opposing side to that of the first and second supports 9A, 9B or below the first and second supports 9A, 9B.

The rod bender 1 includes a rod receiving area RA located between the mobile head 11 and the first and second supports 9A, 9B configured to receive the first rod 5 and the second rod 7.

The mobile head 11 is configured to be displaced towards the first side 51 and in the rod receiving zone 3 to contact the second rod 7 and to apply a force to the second rod 7 to push the second rod 7 towards the first rod 5 to impart a curvature to the second rod 7. The mobile head 11 is configured to be displaced towards the first and second supports 9A, 9B and to pass between the first and second supports 9A, 9B. The mobile head 11 may also be configured to be displaced to pass between the first and second supports 9A, 9B and above or beyond the first and second supports 9A, 9B.

The mobile head 11 is configured to apply a force to the second rod 7 to impart a matching or corresponding curvature of the first rod 5 to the second rod 7.

The mobile head 11 is configured to apply a force to the second rod 7 to push the second rod 7 towards the first rod 5 to impart a curvature of the first rod 5 to the second rod and only generate tensional forces in the second rod 7.

The second rod 7 being more malleable or less hard that the first rod 5 bends under the force applied by the mobile head 11 to adopt the contour (or a similar contour or curve) of the harder first rod 5.

The mobile head 11 includes, for example, a curved, cylindrical or circular surface 21 for contacting the second rod 7. This prevents the second rod 7 being damaged during the bending process. The mobile head 11 can be, for example, a removable head 11 removable from the rod bender 1 to permit different mobile heads 11 having different diameters or contours to be used in the rod bending process. The mobile head 11 comprises or consists of, for example, a metal. The metal can be, for example, a metal of hardness greater than that of the second rod 7.

The rod receiving zone 3 includes a first lateral opening O1 and a second lateral opening O2 permitting the first rod 5 and the second rod 9 to be displaced laterally within the rod receiving zone 3. The first and second lateral openings O1, O2 are directly connected with or directly communicate with the rod receiving zone 3. This, for example, allows the first rod 5 and the second rod 7 to be displaced laterally between the first and second lateral openings O1, O2 and to impart curvatures at different locations along the length of the second rod 7.

Alternatively or additionally, the mobile head 11 may further be configured to be displaced laterally between the first and second lateral openings O1, O2 permitting to impart curvatures at different locations along the length of the second rod 7.

The first support 9A and a second support 9B are immobile and held in a body 17 of the rod bender. The body 17 defines, for example, the rod receiving zone 3 and/or the first and second lateral openings O1, O2.

The supports 9A and 9B are, for example, each received in a bore of complementary shape in the body 17 of the rod bender 1 and are held fixed or anchored in the body 17 during bending of the second rod 7. The first 9A and second 9B supports are, for example, attached immobile to the body 17.

The mobile head 11 is configured to be displaced towards the first 9A and second 9B immobile supports. The mobile head 11 is configured to be displaced linearly towards the first 9A and second 9B support, or configured to be displaced solely linearly towards the first 9A and second 9B support.

The first 9A and second 9B supports are immobile with respect to each other and with respect to the mobile head 11.

The first support 9A and/or the second support 9B may include a curved, cylindrical or circular surface for contacting the first rod 5. The first support 9A and/or the second support 9B may include a body (for example, a metallic body), for example, a cylindrical body. The body or cylindrical body may include an annular depression or groove 19. The first support 9A and/or the second support 9B may, for example, comprise pins, or metallic pins, including the annular depression or groove 19. The metal can be, for example, a metal of hardness greater than that of the second rod 7 and/or the first rod 5.

The body 17 of the rod bender 1 can be configured to receive a plurality of different supports 9A, 9B each having a different outer diameter or width; or each comprising an annular depression or groove 19 having a different depression depth.

The first support 9A and the second support 9B are, for example, substantially aligned at (substantially) the same distance from the mobile head 11. The first support 9A and the second support 9B are, for example, separated by a distance of between 4 and 10 cm, for example, 6 cm.

The mobile head 11 has, for example, a diameter of between 0.5 cm and 2 cm, for example 1 cm. The supports 9A, 9B have an outer diameter between for example 0.25 cm and 1 cm, for example 0.5 cm. This diameter is reduced at the location of the annular depression or groove 19, for example by 25 to 40%. The annular depression or groove 19 may, for example, a radius of curvature identical or slightly larger than a radius of curvature of the first rod 5, for example, between 2.25 mm and 3 mm, for example 2.5 mm or 2.75 mm.

The first rod 5 and/or second rod 7 may have a diameter or width between 4.5 mm and 6 mm, for example, 5 mm, 5.5 mm or 6 mm.

The orthopaedic rod bender 1 may comprise a mechanism M1 to convert a rotational motion into a linear motion to displace the mobile head 11 linearly (or solely linearly) towards the first 9A and second 9B support.

The mechanism M1 may include a threaded shaft 15 extending through a complementary threaded bore in the body 17. The threaded shaft 15 is attached or removably attached to the mobile head 11. A knob 23 can be attached to the threaded shaft and to the mobile head 11 to manually displace the mobile head 11 by rotation of the threaded shaft 15. Alliteratively or additionally, the rod bender 1 may include a motor linked to threaded shaft 15 and/or the mobile head 11 to displace the mobile head 11 in the rod receiving zone 3.

The body 17 may comprises or consists solely of a plastic or a metal, for example, aluminum.

The body 17 can, for example, be a laser cut body. The laser cut body 17 can, for example, define the rod receiving zone 3 and/or the bores for receiving the supports 9A, 9B and/or the threaded shaft 15. The present disclosure also concerns an orthopaedic rod bender system 25 including the above-mentioned orthopaedic rod bender 1, as well as, for example, at least the first rod 5 and/or at least the second rod 7.

The present disclosure also concerns an orthopaedic rod bending method.

The method may comprise the steps of:
  providing an orthopaedic rod bender 1 or system 25 as mentioned above;
  inserting the first rod 5 into the rod receiving zone 3, for example, in contact with the first 9A and second 9B supports;
  inserting the second rod 7 into the rod receiving zone 3 between the first rod 5 and the mobile head 11; and
  displacing the mobile head 11 towards the second rod 7 to contact the second rod 7 and to apply a force to the second rod 7 to push the second rod 7 towards the first rod 5 to contact the first rod to impart a curvature to the second rod 7.

The mobile head 11 applies a force to the second rod 7 to push the second rod 7 towards the first rod 5 to impart a matching curvature or corresponding curvature of the first rod 5 to the second rod 7.

The mobile head 11, for example, applies a force to the second rod 7 to push the second rod 7 towards the first rod 5 to impart a matching curvature or corresponding curvature of the first rod 5 to the second rod 7 while only generating tensional forces in the second rod 7.

During the process to impart a matching curvature or corresponding curvature of the first rod 5 to the second rod 7, the first rod 5 and the second rod 7 may need to be rotated, for example, by 180 degrees, and the above rod bending process repeated. Additionally or alternatively, the first rod 5 and/or the second rod 7 may be displaced laterally in the rod receiving zone 3 (towards opening O1 or OA) and the above rod bending process repeated.

Figures 1B, 1C:
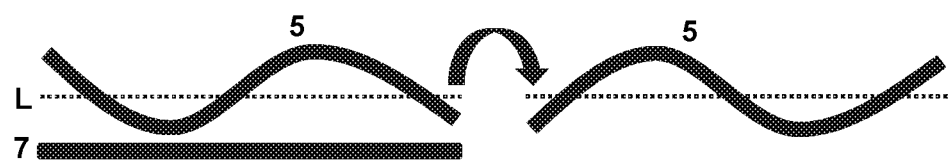
FIG. 1B is shows schematically a first rod having a predefined curvature and a second rod to which a curvature is to be imparted.
FIG. 1C also schematically shows the first rod having a predefined curvature of FIG. 1B after having been rotated by 180° about itself or about longitudinal axis L.
Figure 2A:
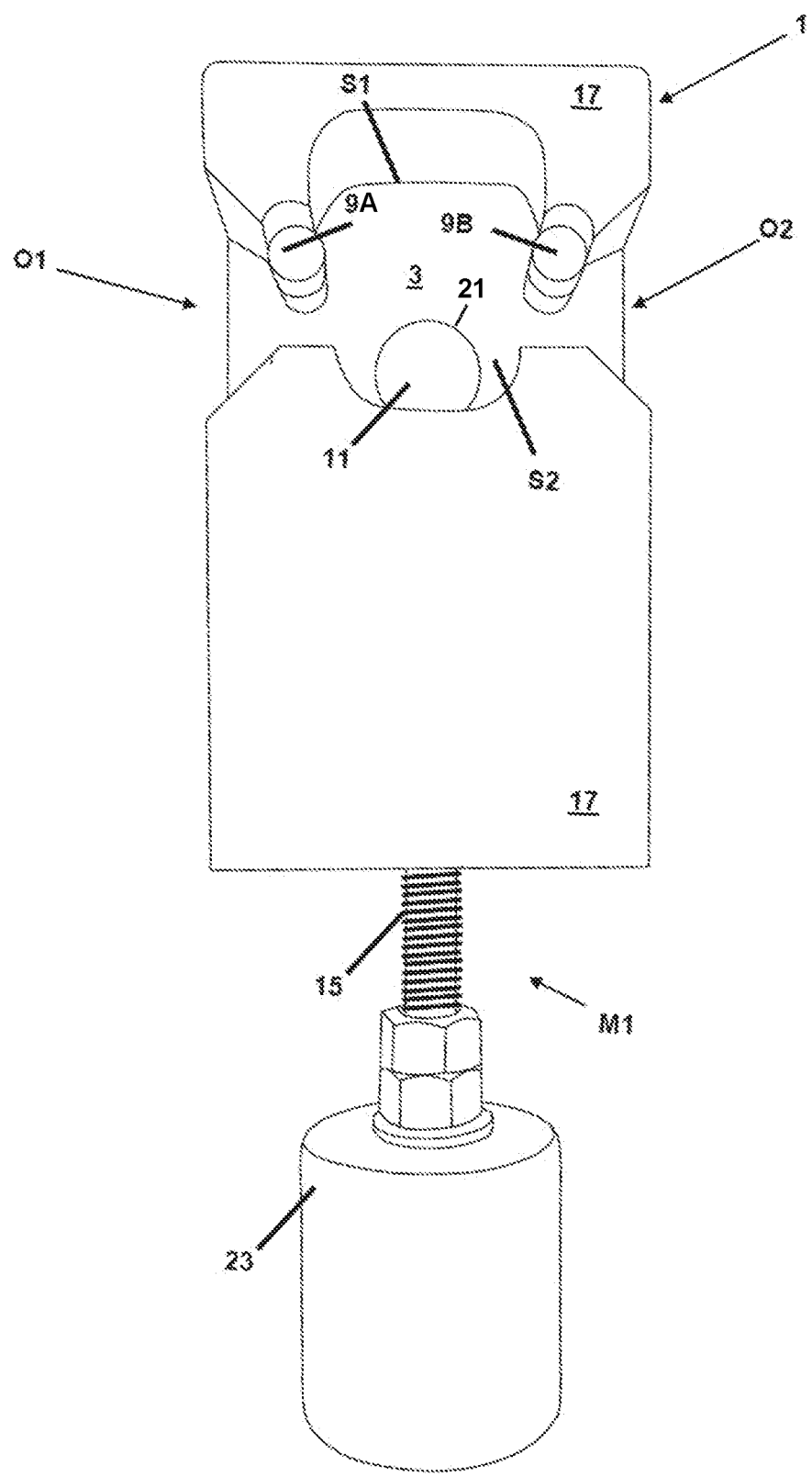
Figure 2B:
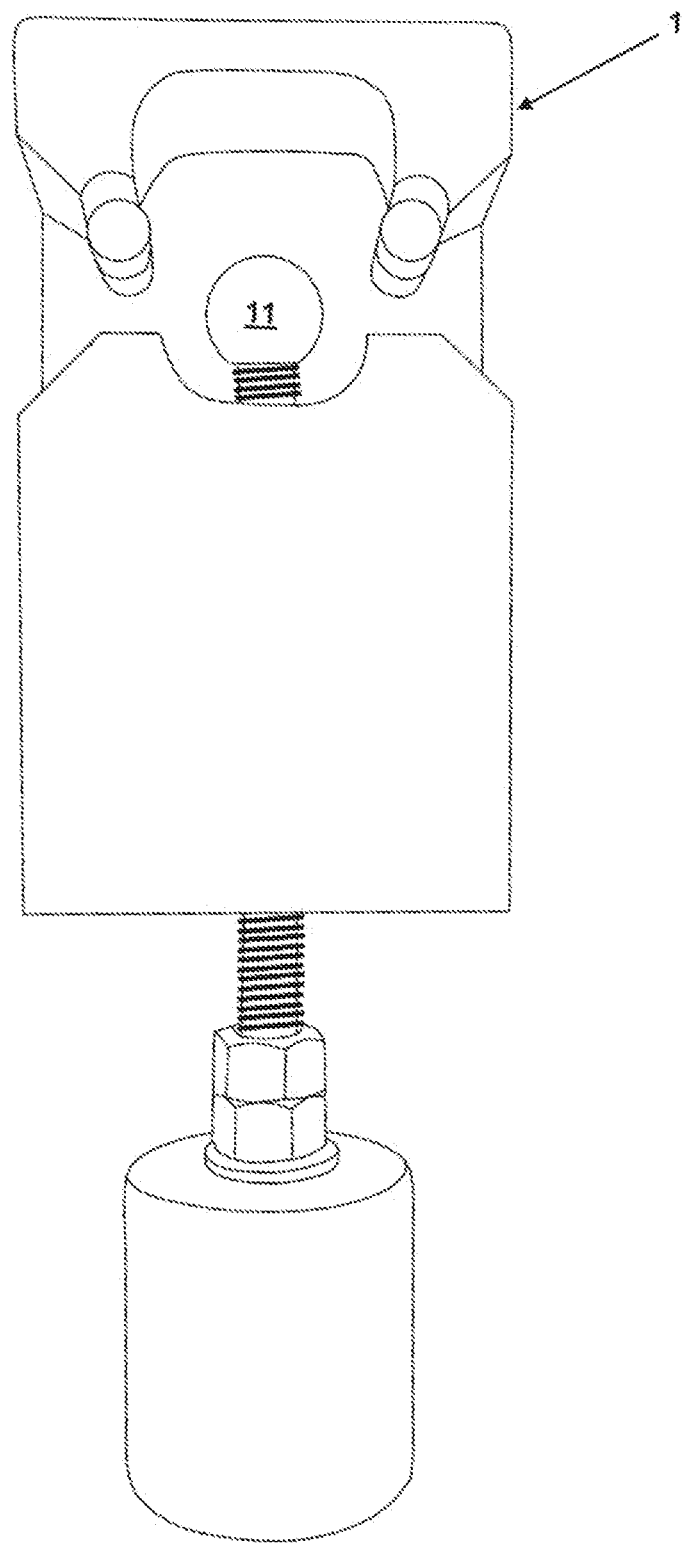
Figure 2C:
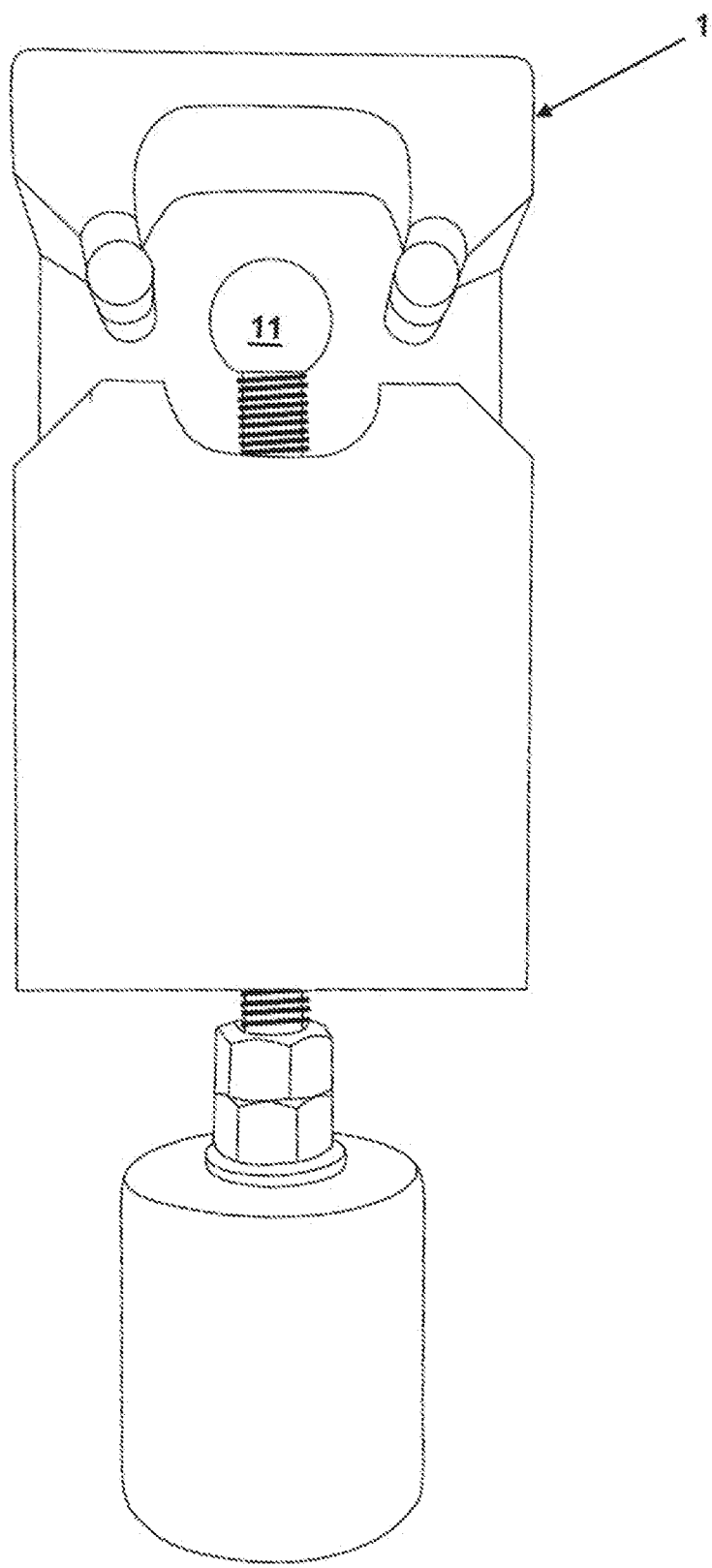
Figure 2D:
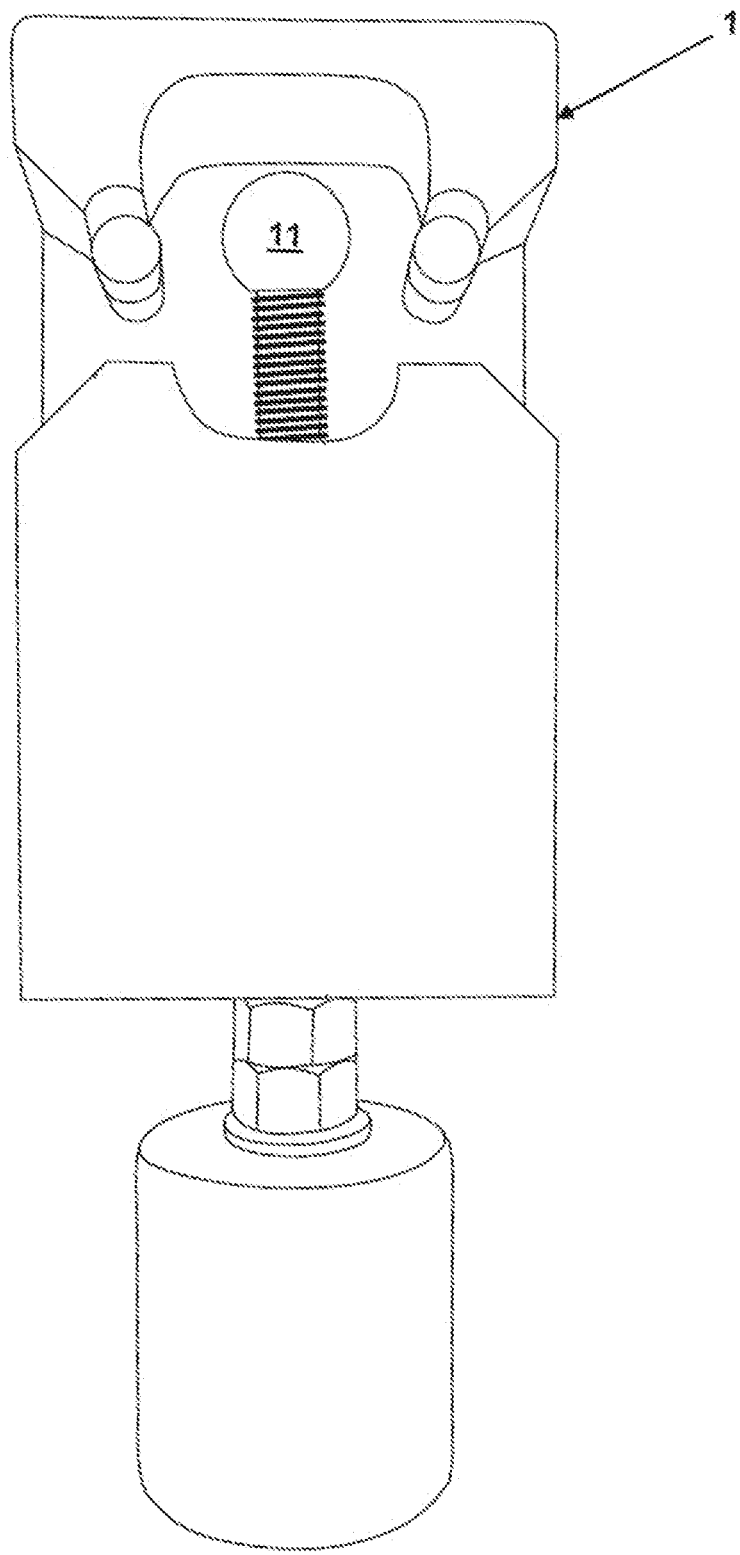

For example, for a first rod 5 shown schematically in FIG. 1B that contains a plurality of curvatures, the first rod 5 (and the second rod 7) can be rotated by 180 degrees about itself or about a longitudinal axis L (the first rod 5 is spun around by 180°) as shown in FIG. 1C and the above rod bending process repeated using the rod bender 1. The first rod 5 and/or the second rod 7 may alternatively or additionally need to be laterally displaced in the rod receiving zone and the rod bender 1.

Consequently, repeating the displacement of the mobile head 11 towards the second rod 7 to contact the second rod 7 and to apply a force to the second rod 7 to push the second rod 7 towards the first rod 5 to impart the curvature of the first rod 5 to the second rod 7 may need to be carried out depending on the complexity of the curvature of the first rod 5.

As previously mentioned, the first rod 5 has a predefined curvature (substantially) corresponding to or matching a curvature linking or passing through heads of a plurality of implanted spinal screw heads.

The method may thus also include the steps of:
  providing the first rod 5;

manually bending the first rod 5 to define a curvature or bending (substantially) corresponding to or matching a curvature linking or passing through heads of a plurality of implanted spinal screw heads; and allowing the material of the first rod 5 to harden.

As mentioned, the first rod 5 comprises or consists solely of a work-hardening material. The first rod 5 may for example comprise or consist solely of aluminum, or copper, or 6061-T6 alloy or 6061-T4 alloy. The second rod 7 may comprise or consist solely of steel, stainless steel or titanium.

Once hardened, the first rod 5 is placed in the rod bender 1 and the rod bending process as described above is carried out to the second rod 7. The method thus provides a rod 7 comprising a replica or a close replica of the curvature of the first rod 5. The curvature (substantially) matches or corresponds to that of the first rod 5.

While the invention has been disclosed with reference to certain preferred embodiments, numerous modifications, alterations, and changes to the described embodiments, and equivalents thereof, are possible without departing from the sphere and scope of the invention. The features of any one of the described embodiments may be included in any other of the described embodiments. Accordingly, it is intended that the invention not be limited to the described embodiments, and be given the broadest reasonable interpretation in accordance with the language of the appended claims.

The invention claimed is:

1. An orthopedic rod bender comprising:
    a rod receiving zone configured to receive a first rod having a predefined curvature and a second rod to which a curvature is to be imparted using the first rod;
    a first support and a second support configured to contact the first rod, the first support and the second support being located on a first side of the rod receiving zone; and
    a mobile head located on a second side of the rod receiving zone opposite the first side, the mobile head configured to displace towards the first side and, in the rod receiving zone, configured to contact the second rod and to apply a force to the second rod to push the second rod towards the first rod to impart a curvature of the first rod to the second rod,
    wherein the rod receiving zone is configured to simultaneously receive the first rod having the predefined curvature and the second rod, the first rod having the predefined curvature being received between (i) the first support and the second support, and (ii) the mobile head, the second rod being received between the first rod having the predefined curvature and the mobile head.

2. The orthopedic rod bender according to claim 1, wherein the mobile head is further configured to apply the force to the second rod to push the second rod towards the first rod to impart a matching or corresponding curvature of the first rod to the second rod.

3. The orthopedic rod bender according to claim 1, wherein the mobile head is further configured to apply the force to the second rod to push the second rod towards the first rod to impart a curvature of the first rod to the second rod and thereby solely generate tensional forces in the second rod.

4. The orthopedic rod bender according to claim 1, wherein the rod receiving zone includes a first lateral opening and a second lateral opening permitting the first rod and the second rod to be displaced laterally within the rod receiving zone.

5. The orthopedic rod bender according to claim 1, wherein the mobile head is configured to be displaced linearly towards the first support and second support.

6. The orthopedic rod bender according to claim 1, further comprising:
    a threaded shaft configured to convert a rotational motion into a linear motion to displace the mobile head linearly towards the first support and the second support.

7. The orthopedic rod bender according to claim 1, further comprising:
    a body defining the rod receiving zone.

8. The orthopedic rod bender according to claim 7, wherein the first support and the second support are fixedly attached to the body.

9. The orthopedic rod bender according to claim 1, wherein the first support and the second support each include a pin having an annular depression or groove.

10. The orthopedic rod bender according to claim 1, wherein the mobile head includes a cylindrical or circular surface for contacting the second rod.

11. The orthopedic rod bender according to claim 1, further comprising:
    a knob attached to the mobile head to manually displace the mobile head, or a motor linked to the mobile head to displace the mobile head.

12. An orthopedic rod bending method performed with the orthopedic rod bender according to claim 1, the method comprising:
    inserting the first rod having the predefined curvature into the rod receiving zone of the orthopedic rod bender, such that the first rod is in contact with the first support and the second support;
    inserting the second rod to which the curvature is to be imparted using the first rod into the rod receiving zone between the first rod and the mobile head of the orthopedic rod bender; and
    displacing the mobile head towards the second rod to contact the second rod and to apply the force to the second rod to push the second rod towards and directly contact the first rod to impart the curvature of the first rod to the second rod.

13. The method according to claim 12, wherein the displacing further comprises:
    forcing the second rod by the applied force to push the second rod towards the first rod to impart a matching or corresponding curvature of the first rod to the second rod.

14. The method according to claim 12, wherein the displacing further comprises:
    applying the force to the second rod to push the second rod towards the first rod to impart a curvature of the first rod to the second rod thereby solely generating tensional forces in the second rod.

15. The method according to claim 12, further comprising:
    rotating at least one of the first rod and the second rod; and
    displacing of the mobile head towards the second rod to contact the second rod and to apply a force to the second rod to push the second rod towards the first rod to impart a further curvature of the first rod to the second rod.

16. The method according to claim 12, wherein the first rod has the predefined curvature corresponding or matching a curvature linking or passing through heads of a plurality of implanted spinal screw heads.

17. An orthopedic rod bender system comprising:
    a first rod having a predefined curvature;

a second rod; and an orthopedic rod bender including
- a rod receiving zone configured to receive the first rod having the predefined curvature and the second rod to which a curvature is to be imparted using the first rod,
- a first support and a second support configured to contact the first rod, the first support and the second support being located on a first side of the rod receiving zone, and
- a mobile head located on a second side of the rod receiving zone opposite the first side, the mobile head configured to displace towards the first side and, in the rod receiving zone, configured to contact the second rod and to apply a force to the second rod to push the second rod towards the first rod to impart a curvature of the first rod to the second rod, wherein the rod receiving zone is configured to simultaneously receive the first rod having the predefined curvature and the second rod, the first rod having the predefined curvature being received between (i) the first support and the second support, and (ii) the mobile head, the second rod being received between the first rod having the predefined curvature and the mobile head.

18. The orthopedic rod bender system according to claim 17, wherein the first rod includes a work-hardening material.

19. The orthopedic rod bender system according to claim 17, wherein the second rod is an inter-vertebral linking rod.

20. The orthopedic rod bender system according to claim 17, wherein the first rod includes at least one of aluminum, copper, 6061-T6 alloy, and 6061-T4 alloy, and wherein the second rod includes at least one of steel and titanium.

* * * * *